United States Patent [19]

Henault et al.

[11] 4,218,297

[45] Aug. 19, 1980

[54] ELECTROCHEMICAL GAUGE FOR OXYGEN HAVING AN INTERNAL REFERENCE AND SOLID ELECTROLYTE

[75] Inventors: Marc Hénault, Gieres; Gérard Vitter, Saint Martin d'Heres, both of France

[73] Assignee: Agence Nationale de Valorisation de la Recherche (ANVAR), Neuilly sur Seine, France

[21] Appl. No.: 910,626

[22] Filed: May 30, 1978

[30] Foreign Application Priority Data

May 27, 1977 [FR] France ............................ 77 16404

[51] Int. Cl.² ........................................... G01N 27/58
[52] U.S. Cl. ............................................. 204/195 S
[58] Field of Search .............................. 204/15, 195 S

[56] References Cited

U.S. PATENT DOCUMENTS

| | | | |
|---|---|---|---|
| 883,170 | 3/1908 | Christy | 204/291 |
| 3,835,012 | 9/1974 | Hemak | 204/195 S |
| 3,883,408 | 5/1975 | Kim et al. | 204/195 S |
| 4,045,319 | 8/1977 | DePortes et al. | 204/195 S |
| 4,063,897 | 12/1977 | Aoki | 204/195 S |
| 4,065,372 | 12/1977 | Hacker et al. | 204/195 S |
| 4,088,543 | 5/1978 | Ruka | 204/195 S |
| 4,098,650 | 7/1978 | Sayles | 204/195 S |
| 4,129,491 | 12/1978 | Obiaya | 204/195 S |

Primary Examiner—G. L. Kaplan
Attorney, Agent, or Firm—Weiser, Stapler & Spivak

[57] ABSTRACT

The invention provides an electrochemical gauge for measuring oxygen pressures having an internal reference and a solid electrolyte. The internal reference is provided by a mixture of lead and lead oxide forming a redox couple. The electrochemical gauge may be used to determine the ratio of the partial pressure of CO to that of $CO_2$ in equilibrating combustion gases.

16 Claims, 6 Drawing Figures

ELECTROCHEMICAL GAUGE FOR OXYGEN HAVING AN INTERNAL REFERENCE AND SOLID ELECTROLYTE

BACKGROUND OF THE INVENTION

This invention relates to an electrochemical device for the measurement of oxygen pressures and more particularly concerns as electrochemical oxygen gauge of the type having an internal reference pressure and solid electrolyte.

The invention also concerns the application of such gauges to the measurement of partial pressures of oxygen, particularly in gazeous mixtures, and notably in combustion gases. It further concerns their application to the determination of the relative quantities of other gases in these mixtures, particularly with a view to the regulation of their composition.

The gauges of this type comprise an electrolyte in contact with two electrical conductors located respectively in different environments comprising oxygen.

These conductors are comparable in their operation to electrodes and form with the electrolyte a chain which can be considered as an electrochemical system.

One of the electrodes, the reference electrode, is situated in a compartment containing a chemical system which establishes within that compartment an oxygen pressure which acts as the reference pressure. This system, which will be designated hereinafter by the expression "internal reference", is generally made up either by a gaseous mixture such as an oxygen-gas, $CO$-$CO_2$ or $H_2$-$H_2O$ mixture, by pure oxygen, by a metal-metal oxide mixture or even by a mixture of two oxides of the same metal.

The reference electrode is in contact with an electrolyte made up by an ionic conductor capable of permitting the transfer only of oxygen ions. This electrolyte can be composed of a ceramic oxide or a vitreous phase having true ionic conduction, for example, it may be a solid solution of oxides depleted in oxide ions and having the fluorite structure, or a vitreous phase such as that described by D.YUAN and F. A. KROEGER in J. Electrochem. Soc. 118, 841 (1971).

The second electrode, the measurement electrode, is also in contact with the electrolyte but lies outside the reference compartment, and is placed in the oxygen-containing atmosphere that is desired to analyse. The electrode together with the atmosphere under test constitutes the measurement compartment.

The presence of oxygen in the oxide state an oxygen in the reduced state in contact with the electrodes of each of the reference and measurement compartments leads to a reaction at these electrodes, and thus to a potential difference being established between them. This potential difference obeys the Nernst equation, according to which:

$$E = RT/4F \, Ln \, P_{O_2 ref}/P_{O_2 mes}.$$

In this formula, the various symbols used have the following meanings:
E = electromotive force in volts
R = ideal gas constant
T = temperature in degrees Kelvin
F = Faraday number
$P_{O_2 \, ref}$ = oxygen pressure in the reference compartment
$P_{O_2 \, mes}$ = oxygen pressure in the measurement compartment If the reference oxygen pressure and the temperature are constant, the reading of the potential difference is a measure of the partial pressure of oxygen in the measurement compartment.

Furthermore, it is known that this partial pressure of oxygen in a gaseous mixture in an oxidation-reduction equilibrium is related by the law of mass action to partial pressures of other gaseous constituents of the mixture. Measurement of the partial pressure of oxygen as described hereinbefore can therefore provide a means of discovering the partial pressures of the other constituents of the mixture and by this means the composition of the mixture can be determined.

The significance of such an application of the gauge of the invention is evident, especially for the measurement of the concentration of the principal constituents of a combustion gas. It enables the composition of the mixture of combustive and combustible gaseous components (the combustive-combustible mixture) to be regulated so as to obtain better performance. In addition, it may be possible to effect regulation of the mixture so as to lower the amount of toxic gases formed from the combustion gas, and in particular to lower the level of carbon monoxide.

The partial pressure of oxygen in the system $CO + \frac{1}{2} O_2 \rightleftarrows CO_2$ is related under conditions of thermodynamic equilibrium to that of carbon monoxide (CO) and carbon dioxide ($CO_2$) by the law of mass action so that by adjusting the partial pressure of oxygen appropriately the partial pressure of CO can be lowered.

However, to perform regulations of this type it is necessary to have a gauge of high performance which in particular must be capable of giving very accurate measurements of the partial pressures of the constituents of the gas being analysed. Moreover, development of oxygen gauges on a commercial scale, especially when they are intended for the above applications, requires the gauges to be compact and capable of operation without needing additional equipment. However, until now gauges intended for the applications described above do not fulfil these needs in a satisfactory manner.

Generally the known gauges utilize air to establish a reference pressure, and to improve the accuracy of the measurements gas with a known partial pressure of oxygen is circulated within the reference compartment. These gauges are extremely inconvenient and do not give sufficiently precise results.

Other known gauges are those in which the internal reference is a metal-metal oxide mixture. Those gauges of this type which employ a palladium (Pd): palladium oxide (PdO) redox system, corresponding to the equilibrium $Pd + \frac{1}{2} O_2 \rightleftarrows PdO$, possess very interesting properties when compared with gauges containing other metal-metal oxide mixtures as the internal reference. In particular they enable accurate measurements of oxygen partial pressures to be obtained. However, even though the use of such a redox system gives the gauges some useful properties, it has not proved entirely suitable as an internal reference in the aforementioned applications, and it is particularly inconvenient for the determination of the relation between the partial pressures of CO and $CO_2$—that is to say $P_{CO}/P_{CO_2}$,—in combustion gases. The temperature dependance of this redox system when employed as an internal reference is such that the voltages produced by gauges using the redox system vary considerably with temperature.

Thus, measurements taken when the operating temperature is variable do not lead directly to the actual composition of the gas, and particularly do not provide the actual value of the ratio of the partial pressures of CO and $CO_2$. In order to try to alleviate this problem and obtain constant voltage outputs despite possible variations in operating temperatures it is necessary to equip gauges employing this type of system with some means of temperature regulation. This makes the gauges unsuitable because of their increased size and the increased overall cost of the equipment.

SUMMARY OF THE INVENTION

However, it has now been established that it is possible to overcome, at least to a large extent, the disadvantages of such known gauges by using as the internal reference a new redox couple of the metal-metal oxide type. The invention seeks to provide a new redox system which may be useful in providing an internal reference for an oxygen gauge.

According to another aspect the invention provides an oxygen gauge equipped with such an internal reference and several methods of construction of such a gauge.

According to a further aspect of the invention, there is provided a method of using such gauges in the determination of the composition of gaseous mixtures, particularly in determining the composition of combustion gases and especially in the determination of the $P_{CO}/P_{CO2}$ ratio. The invention also concerns the application of the gauges to the regulation of the composition of gaseous fuel mixtures and of gaseous combustive-combustible mixtures.

According to the invention there is provided a redox system capable of establishing an internal reference of an electrochemical gauge for determining oxygen pressures, which redox system comprises a mixture of lead (Pb) and lead oxide (PbO) capable of reacting according to the equilibrium:

$$Pb + \tfrac{1}{2}O_2 \rightleftharpoons PbO$$

This Pb:PbO redox system is capable of providing, at a given temperature, a well defined oxygen pressure which can be used as a reference pressure. It has the advantages of being in thermodynamic equilibrium over a range of temperatures of from about 400° to 1500° C., and of rapidly returning to a new equilibrium state when the temperature varies. It can thus be used without any inconvenience in conditions where the operating temperature is not stable.

The study of the Pb:PbO system by the inventors has shown that it is of particular interest for use as an internal reference. In fact, the characteristics of its equilibrium constant are such that the oxygen pressure that it establishes is dependant only on the temperature, but the function defining the variation of this oxygen pressure with temperature is practically identical to that defining the oxygen pressure associated with the equilibrium:

$$CO + \tfrac{1}{2}O_2 \rightleftharpoons CO_2$$

It follows that the voltages provided by oxygen gauges comprising the Pb: PbO system as internal reference in measuring the $P_{CO}/P_{CO2}$ ratio will in practice be a function only of that ratio and insignificantly affected by variations in the operating temperature.

These properties of the Pb:PbO redox couple make it particularly suitable for use as the internal reference in an oxygen gauge, particularly where the gauge is intended to measure the partial pressures of oxygen resulting from the $CO/CO_2$ equilibrium to determine the value of the $P_{CO}/P_{CO2}$ ratio under equilibrium conditions.

The invention therefore provides an oxygen gauge comprising, as the internal reference, a Pb:PbO system. The gauge comprises a hermetically sealed internal reference compartment containing a solid or liquid material selected from the group consisting of lead, lead oxide and mixtures of these compounds, this material being capable of establishing the reference partial pressure of oxygen in the gauge.

The reference compartment is defined at least in part by a solid electrolyte of the oxide type and comprises an electrode in electrical contact with the interior of the compartment, with the reference material and with the said electrolyte.

The electrolyte is furthermore in electrical contact with a measurement electrode external to the reference compartment.

According to a preferred construction, the oxygen gauge of the invention is protected by a cover member defining around the measurement electrode a space protected from possible disturbances in the external atmosphere being analysed, this cover having an opening to enable the atmosphere being analysed to enter this space thus defined.

A gauge of this type has been found to perform remarkably well. In particular, because of the stability and rapidity with which the internal reference reaches equilibrium, the gauge provides very precise measurements of oxygen pressures, especially in gaseous mixtures, and operates in an extremely satisfactory manner over a range of temperatures of about 400° C. to 1100° C. In addition, a considerable economic advantage is that the life of the gauge can be long because the internal reference may be regenerated. Using relatively low recharging voltages it is possible to bring about this regeneration by electrolytic reduction of the oxide, or electrolytic oxidation of the metal, in the internal reference, when the operating conditions of the gauge have resulted in the transformation of either of the constituents of the Pb:PbO mixture or where one of these constituents has been formed in a proportion which prevents accurate functioning of the gauge.

According to a preferred aspect of the invention, the oxygen gauge preferably comprises a reference compartment in the form of a hermetically sealed tube or case of which the walls are made up totally or partially by the electrolyte. This compartment is filled, at least in part, by a suitable mixture of Pb and PbO to set up a redox couple corresponding to the equilibrium:

$$Pb + \tfrac{1}{2}O_2 \rightleftharpoons PbO$$

and also to provide, at a given temperature, a reference oxygen pressure.

The reference compartment also comprises an electrical conductor, or reference electrode, maintained in contact with the internal reference and the electrolyte. This electrode is made up of one or more metals or non-oxidizable alloys and/or one or more oxides which are electrically conductive under the operating conditions of the gauge. It can advantageously be copper, and this is particularly appropriate when operating under reducing conditions, or platinum, which is particularly suitable for oxidizing conditions. Alternatively the electrode may be made up of conductive elements juxtaposed so as to provide electrical continuity, and particularly it may be steel and copper bound, for example, by a conducting glass and/or lanthanum chromite.

The solid electrolyte of the oxide type which may be used in the gauge, to form at least a part of the walls of the reference compartment, possess only ionic conductivity. Electrolytes of this type, which may be used in oxygen gauges operating in a convenient range of oxygen pressures both for reference and measurement, are well known to those skilled in the art. Amongst the oxides which can be used as the electrolyte, those formed by stabilized zirconia, by solid solutions of zirconia and yttrium oxide, or even by solid solutions of oxides based on thoria are particularly useful.

The solid electrolyte is advantageously employed in a form sufficiently water and air tight in itself, and to achieve this it is desirable to employ a material obtained by sintering or by shaping a single crystal.

As indicated hereinbefore, the reference compartment is hermetically sealed. It is necessary to ensure precision in the measurements made to prevent any constituents of the external atmosphere from entering the reference compartment. It is equally necessary that the compartment, and consequently also the redox mass that it contains, are maintained at a uniform temperature. Indeed it is desirable to avoid any variation in the oxygen pressure fixed by the redox system resulting from the existence of a temperature gradient inside the compartment, and to prevent condensation of the oxide or the metal, which at a given temperature, will be sufficiently volatile to evaporate and condense in the coldest part of the reference compartment.

So as to ensure a hermetic seal, the reference compartment is preferably closed with an appropriate material that will seal the walls defining the compartment. The tube or case is also sealed where the reference electrode leaves the compartment, and also between the different portions which may make up the case. This sealing may be effected with a material which remains sufficiently durable at the working temperatures of the gauge and is sufficiently impermeable to oxygen. Amongst the materials which may be used, it is preferred to use a glaze of pyrex glass, or a glass having a coefficient of expansion similar to that of the case.

The oxygen gauge further comprises a measurement electrode external of the reference compartment and maintained in contact with the electrolyte. This is advantageously formed of a metal, preferably platinum or an alloy which will not oxidize at the operating temperatures, and/or an electrically conductive oxide such as lanthanum chromite.

The gauges constructed in this way are particularly precise and sensitive. Their response times to the variation in the composition of the gas being studied is very short, and furthermore they have a remarkable mechanical strength and a high resistance to thermal shocks. These advantages can still be obtained even when the gauges of the invention are made very small. Miniaturized gauges advantageously comprise a reference compartment of a small volume compared with the thickness of the walls defining the compartment. Such gauges are remarkably resistant to high pressures for periods of time as long as several hours and will still function satisfactorily after the pressure has been reduced. In addition, the miniaturization of the gauges of the invention makes it possible to establish an isothermal reference compartment an so remove errors resulting from temperature gradients, which is difficult to achieve with gauges having a larger volume.

According to a further advantageous aspect of the invention, the measurement electrode of an oxygen gauge is protected so as to avoid a forceful sweeping by a cover so as to reduce forceful blasts of the gas being analysed on the measurement electrode, while still permitting the gases to reach the electrode. Such covers may be used in connection with oxygen gauges in general, and particularly with air gauges, as well as with the gauges of this invention.

The cover can be formed as a cylinder, or in a similar shape, positioned around the measurement electrode. It is preferably formed from an alloy which will not oxidize under the operating conditions of the gauge, and for example may be formed from stainless steel.

By using the cover, the constituents of the mixture being analysed are in equilibrium during the measurement, or at least very close to equilibrium, so that the law of mass action applies to them directly or can be applied to them in a reproducable manner. Moreover, the presence of the cover around the measurement electrode enables the movement of the gas being analysed to be reduced to very low values, so that the mechanical abrasion of the electrode by the gases, and any particulate solids that they contain, is practically eliminated. The cover can also be used to advantage to reduce the quantity of gas coming into contact with the measurement electrode, and therefore to reduce the quantity of impurities liable to cause its deterioration.

In this way it is possible to reduce the risk of metal less from the electrode due to the action of impurities and the covering of the electrode by a skin which might hinder the oxygen contained in the gas being tested from contacting directly with the electrolyte and thus increasing the response time of the gauge as a result of the poisoning of the measurement electrode.

As a result of their remarkable performance, and particularly their great accuracy, the gauges of the invention enable the partial pressure of oxygen in a gaseous sample to be determined with great accuracy, and thus enables the composition of that sample to be determined and regulated. In particular, as indicated hereinbefore, the gauges of the invention are particularly appropriate for measuring the ratio $P_{CO}/P_{CO2}$ in combustion gases. The invention extends to the application of gauges of the invention to the determination of the concentration of CO and $CO_2$ in combustion gases.

Test measurements have shown that the output voltages from the gauges of the invention are practically constant for a given $P_{CO}/P_{CO2}$ ratio in the range of about $10^{-2}$ to 1 over a temperature interval that may be varied between about 400° and 1100° C. These measurements, which for practical purposes only depend upon the ratio $P_{CO}/P_{CO2}$, can be utilized directly without correction for temperature to regulate the composition of a combustion gas, the voltages provided by the gauge being employed as the signal to effect regulation. This regulation is preferably used to obtain the desired optimum composition for the combustible-combustive mixture so as to reduce the level of carbon monoxide in the combustion gases to the required standards.

It is thus possible to regulate combustive-combustible mixtures in a simple and economic manner, especially in engines or in burners so as to improve their efficiency—which is demonstrated in energy saving—and to reduce pollution.

BRIEF DESCRIPTION OF THE DRAWINGS

The invention will now be described in more detail, although by way of illustration, with reference to the accompanying drawings, in which.

DESCRIPTION OF THE PREFERRED EMBODIMENTS

Figure 1:
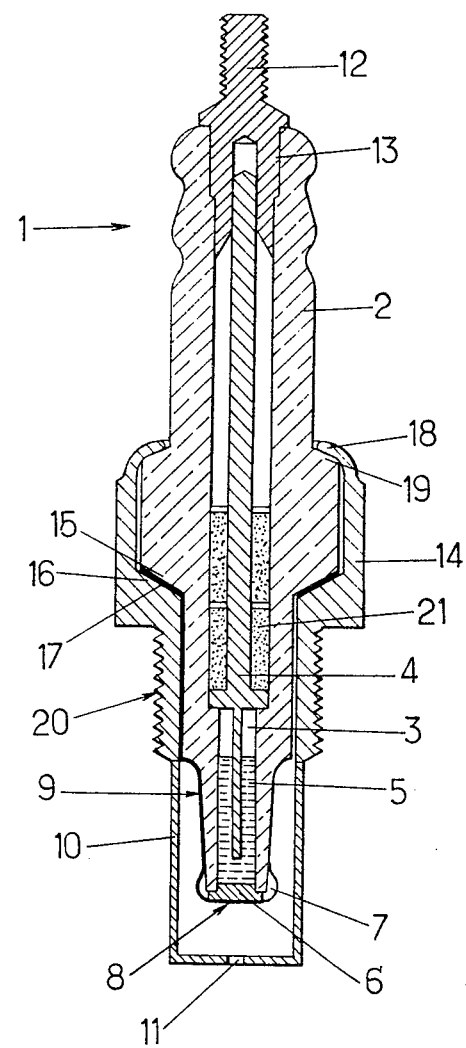
FIG. 1 is a part-cutaway schematic view of a gauge constructed according to a preferred aspect of the invention.

FIG. 1 shows a gauge 1 having a small overall volume. This gauge essentially comprises an insulator 2 formed of aluminium or an analogous material provided with an axial bore defining the reference compartment 3. A copper electrode 4 is located axially within compartment 3. This compartment 3 is closed in a water and air tight manner by means of cement 21 compressed between electrode 4 and insulator 2, so as to form a reference compartment of small volume.

One of the extremities of the electrode is embedded in a mixture of Pb and PbO used to form the internal reference 5 and occupying a part of the reference compartment so as to leave a free space to allow expansion of the Pb-PbO. This Pb-PbO mixture is maintained in the end portion of compartment 3 by a quantity of electrolyte 6 made up of stabilized zirconia which acts as sealant. The electrolyte 6 is sealed on the extremity of the insulator 2 by a glazed cement joint 7. The electrolyte bears on its outside surface a layer of porous platinum 8 which is maintained in contact with the electrolyte to constitute the measurement electrode, and this is joined to a metallic casing 14 by a platinum strip 9.

The corresponding extremity of insulator 2 is protected by a cowel or cover 10 of stainless steel provided with an aperture 11 to allow passage of the gas to be analysed.

The other extremity of reference electrode 4 is set into the base of a threaded pin 12 held in place in the insulator 2 by a sealant 13.

The insulator 2 is held in a metallic socket or casing 14, which acts as a support, by a shoulder 15 abutting against a corresponding surface 16 of the casing with an impervious ring of conductive material 17 therebetween to establish electrical contact between the platinum strip 9 and the body of the casing 14. The upper edge of the casing 18 is formed to contact the upper portion of a boss 19 on the insulator.

Finally, the casing 14 is threaded at 20 so that it can be mounted in a correspondingly threaded bore in the wall of the enclosure or container of the gas to be analysed.

Figure 2:
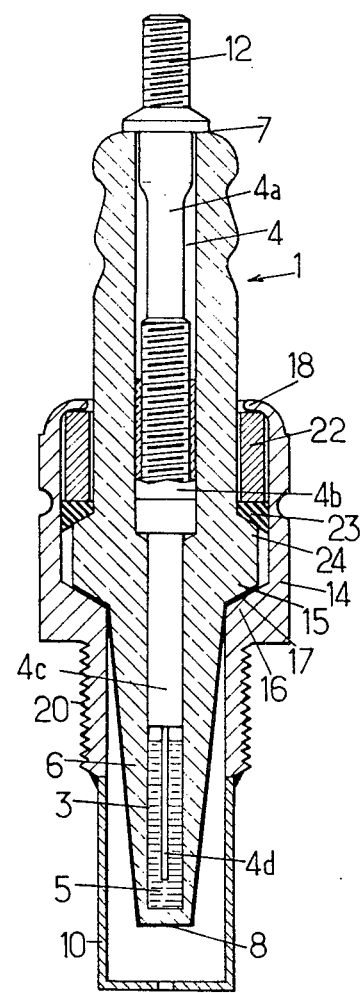
FIG. 2 is a part-cutaway schematic view of an alternative gauge of the invention.

Another form of the gauge of the invention is shown in FIG. 2. In this figure and the following figures, the reference numbers previously used in relation to FIG. 1 designate the same elements.

In this method of construction the electrolyte 6 constitutes the tube or case defining the internal reference compartment filled in part by a mixture Pb and PbO. The axial bore of the electrolyte case contains the electrode 4 which is formed of a steel bar 4a bonded by means of a glass conductor 4b to a copper bar 4c occupying the available space in the bore and extending as a copper pin 4d of which a part is embedded in the mass constituting the internal reference so as to leave a free space to permit expansion of the Pb: PbO mixture.

The measurement electrode comprises a skin of porous platinum deposited on the electrolyte.

The gauge 1 is mounted in a casing 14 of which the upper edge is located at 18 on a bracing ring 22 which in turn rests on an annular impervious joint 23 which is located on a shoulder 24 of the gauge.

Figure 3:
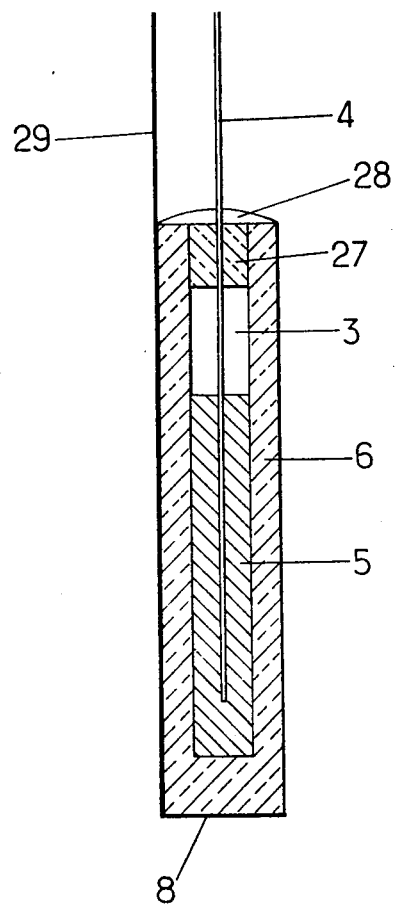
FIGS. 3 and 4 are each cross-sectional schematic views of further examples of gauges constructed according to the invention.

According to a different mode of construction, shown in FIG. 3, the reference compartment 3 of the gauge of the invention is defined by a tube 2 of which the walls are made up by an electrolyte 6 of stabilized zirconia. This tube is closed at its upper end by a plug 27 also formed from stabilizer zirconia which is sealed in the tube by a glaze 28, this latter also assuring a water an air tight seal around the copper reference electrode 4. The tube of electrolyte bears on its outer surface a layer of porous platinum 8 which forms the measurement electrode. A platinum wire 29, which acts as the connection for the potential of the measurement electrode 8, is maintained in electrical contact with this electrode.

Figure 4:
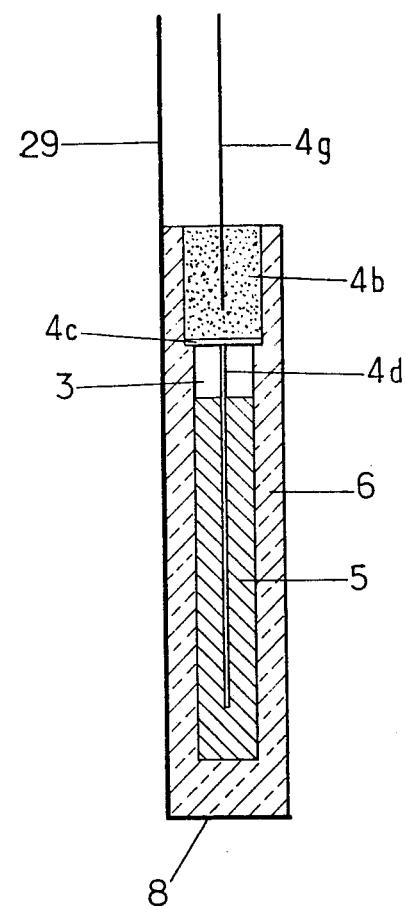

In a variation of this last method of construction shown in FIG. 4, the reference electrode 4 is formed from a platinum wire 4g joined by means of a glass conductor 4b to a copper plate 4c occupying the available space in the bore defined by the electrolyte tube 6 and extending as a copper pin 4d, the end of which is embedded in the mass constituting the internal reference. The glass conductor 4b simultaneously forms a water and air tight closure for reference compartment 3 and makes an electrical connection between the platinum wire 4g, of which a portion is embedded in the glass, and the copper plate 4c. This glass conductor 4b can be made up of a mixture of 70% of glass powder sold under the Trade Mark SOVIREL Type 99150 together with 30% of copper powder.

A miniaturized gauge conforming to the design shown in FIGS. 3 and 4 has been made having a zirconia electrolyte tube of 12 mm height and 2 mm exterior diameter. The useful volume for the internal reference of such a gauge is about 10 $mm^3$.

Figure 5:
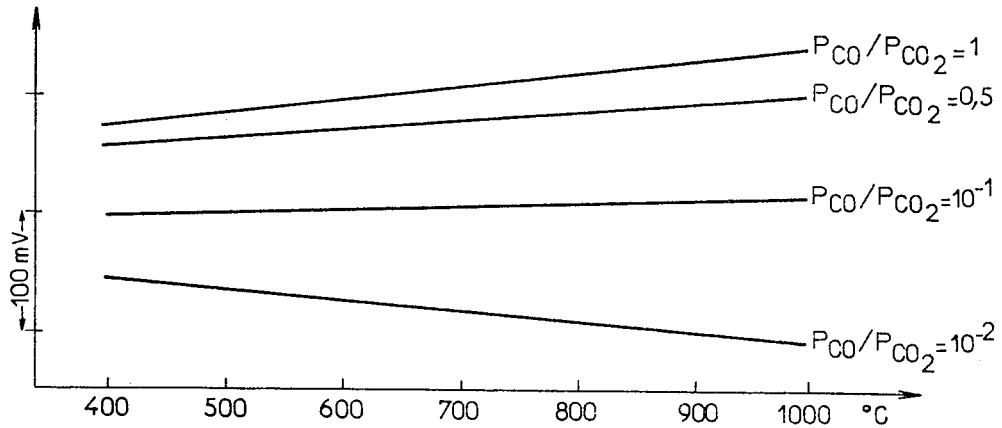
FIG. 5 is a graph showing the variation of e.m.f. for a gauge of the invention with temperature for various ratios of partial pressures CO and $CO_2$ ($P_{CO}/P_{CO_2}$)

To test the performance of the gauges of the invention shown in FIGS. 1 and 2, the variation of the output voltages of the gauges as a function of temperature, for given $P_{CO}/P_{CO_2}$ ratios, has been determined. The results obtained are shown in FIG. 5 which comprises curves representing the variation in voltage expressed in mV (indicated on the ordinate) as a function of temperature in °C. (on the abscissa) for a series of $P_{CO}/P_{CO_2}$ ratios, one curve being shown for each ratio tested. It is evident from an examination of the curves shown in FIG. 5 that over the temperature range tested $-400°$ to $1000°$ C.—the voltages produced by the gauges are for practical purposes unaffected by the operating temperature for partial pressure ratios of carbon monoxide and carbon dioxide varying between 1 and $10^{-2}$. These results are particularly remarkable in the case of a ratio $P_{CO}/P_{CO_2} = 10^{-1}$ in the gas analysed.

Figure 6:
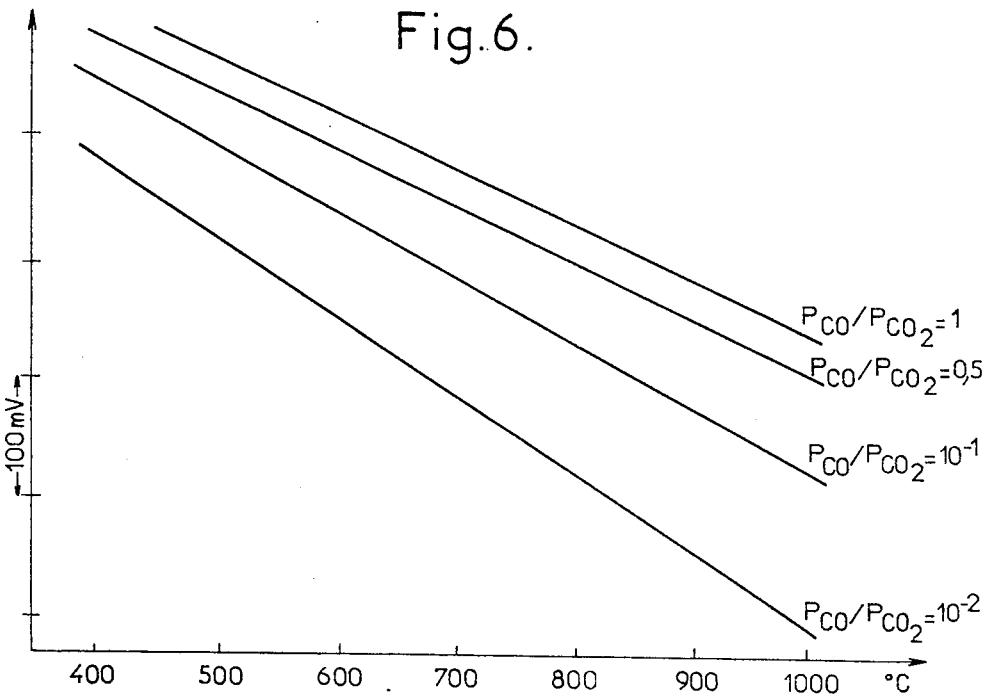
FIG. 6 is a similar graph to FIG. 5, but showing the results obtained with a prior art gauge using air to provide a reference.

A comparison of these results with those shown in FIG. 6, which show the corresponding curves obtained under the same conditions with a gauge having an air reference, show clearly the advantageous effects resulting from the use of a Pb: PbO mixture as the internal reference in an oxygen gauge. It is clear from an examination of the curves shown in FIG. 6 that the voltages produced by the prior art gauges are extremely sensitive to the operating temperature, in complete contrast to the gauges of the present invention.

As indicated hereinbefore, it is necessary if the disadvantages of the prior art gauges are to be reduced for additional equipment to be provided for temperature regulation, which is extremely inconvenient from a practical point of view.

The above results demonstrate very effectively the qualities of the gauges of the invention as devices for measuring the ratios of partial pressures of carbon monoxide and carbon dioxide in combustion gases. In order to investigate in more detail the effectiveness of gauges of the invention at regulating the composition of combustion gases and thus of combustible-combustive mixtures, automobiles having carburetors have been equipped with gauges of the invention. The electrical signal provided by these gauges, located so as to analyse exhaust gases, is used to regulate the fuel/air mixture. The results obtained from these tests show that the fuel consumption of the automobiles was reduced by 7% with a carbon monoxide level in the exhaust gases of the order of 0.5%.

Having regulated the composition of the fuel-air mixture, in order to further diminish the pollutant affects of the engine it is possible using known techniques to circulate the exhausted combustion gases over catalysts, known by those skilled in the art as triple effect catalysts, to eliminate the residual pollutants.

We claim:

1. In an electrochemical gauge for measuring partial pressures of oxygen, said gauge comprising a solid electrolyte and an internal reference, the improvement whereby the internal reference consists essentially of a lead: lead oxide redox couple.

2. Electrochemical gauge for measuring oxygen pressures, having an internal reference and a solid electrolyte, comprising an hermetically-sealed internal reference compartment containing a material selected from the group consisting of lead, lead oxide and mixtures thereof to establish the reference partial pressure of oxygen in the gauge, the reference compartment being defined at least in part by a solid electrolyte of the oxide type and containing an electrode in electrical contact with the interior of the compartment as well as with the reference material and the said electrolyte, the latter also being in electrical contact with a measurement electrode external to the reference compartment.

3. Gauge according to claim 2, which is protected by a cover defining at least around the measurement electrode a space protected from possible disturbances in the external atmosphere being analysed, this cover incorporating, at the cover's extremity only, an aperture permitting the atmosphere being analysed to enter the said space.

4. Gauge according to claim 2, wherein the reference compartment comprises a cavity defined by walls made up wholly by the electrolyte.

5. Gauge according to claim 2, wherein the reference compartment, including the position where the reference electrode leaves the reference compartment, is hermetically sealed by the closure of the reference compartment with a material sealed to the walls defining the compartment.

6. Gauge according to claim 2, wherein the reference electrode is formed of a metal or alloy which does not oxidize under the operating conditions of the gauge and/or of one or more electrically conductive oxides.

7. Gauge according to claim 2, comprising an external electrical conductor positioned over at least portions of, and in electrical contact with, the external surface of the electrolyte and formed of a metal or alloy which does not oxidize under the operating conditions of the gauge and/or of one or more electrically conductive oxides.

8. Gauge according to claim 2, wherein the reference compartment comprises a cavity defined by walls only selected portions of which are made up by the electrolyte.

9. Gauge according to claim 8, wherein those portions of the walls which are not made up by the electrolyte are made up by an insulating material.

10. Gauge according to claim 9, wherein only the extremity of the gauge is made up by the electrolyte.

11. Gauge according to claim 2, wherein the reference electrode comprises a metal wire joined by a glass conductor to a metal plate, and a metal pin which is connected to the metal plate and which extends from the metal plate into the internal reference.

12. Gauge according to claim 2, wherein the volume of the reference compartment is smaller than the volume of the walls defining the reference compartment.

13. Gauge according to claim 2, wherein the reference compartment is approximately 12 mm in height and 2 mm in exterior diameter.

14. Gauge according to claim 2, wherein the volume of the reference compartment is approximately 10 mm$^3$.

15. Electrochemical gauge for measuring oxygen pressures, having an internal reference and a solid electrolyte, comprising
a reference compartment containing a material selected from the group consisting of lead, lead oxide and mixtures thereof to establish the reference partial pressure of oxygen in the gauge,
the reference compartment comprising a cavity defined by walls made up by a solid electrolyte of the oxide type,
a reference electrode, formed of a metal or alloy which does not oxidize under the operating conditions of the gauge and/or of one or more electrically conductive oxides, which reference electrode is in electrical contact with the interior of the compartment as well as with the reference material and the electrolyte, and
a measurement electrode comprising an electrical conductor, external to the reference compartment, positioned over at least portions of, and in electrical contact with, the external surface of the electrolyte, formed of a metal or alloy which does not oxidize under the operating conditions of the gauge and/or of one or more electrically conductive oxides,
wherein the reference compartment, including the position where the reference electrode leaves the reference compartment, is hermetically sealed by the closure of the reference compartment with a material sealed to the walls defining the compartment.

16. Gauge according to claim 15, which is protected by a cover defining at least around the measurement electrode a space protected from possible disturbances in the external atmosphere being analysed, this cover incorporating at its extremity only, an aperture permitting the atmosphere being analysed to enter the space.

* * * * *